United States Patent [19]

Reiss

[11] 4,225,412
[45] Sep. 30, 1980

[54] APPARATUS FOR SEPARATING NEUTRAL MOLECULES USING A BIPOLAR MEMBRANE AS A MOLECULAR SIEVE

[75] Inventor: Howard Reiss, La Jolla, Calif.

[73] Assignee: Occidental Research Corporation, Irvine, Calif.

[21] Appl. No.: 966,196

[22] Filed: Dec. 4, 1978

[51] Int. Cl.³ .............................................. C25B 13/02
[52] U.S. Cl. ................................ 204/301; 204/180 R; 204/180 P; 204/296; 210/321 R; 210/490; 210/500 M; 521/27
[58] Field of Search ................... 204/301, 296, 180 R, 204/180 P; 521/27; 264/308; 429/2; 210/490, 500 M, 321 R

[56] References Cited

U.S. PATENT DOCUMENTS

| | | | |
|---|---|---|---|
| 3,098,802 | 7/1963 | Beer | 204/1 |
| 3,510,417 | 5/1970 | Mizutani et al. | 204/180 P |
| 3,510,418 | 5/1970 | Mizutani et al. | 204/180 P X |
| 3,654,125 | 4/1972 | Leitz | 204/301 |

Primary Examiner—Arthur C. Prescott
Attorney, Agent, or Firm—Robert J. Baran; Barry A. Bisson; William G. Lane

[57] ABSTRACT

A monolithic bipolar membrane having elastic properties is immersed in a polar solvent or an electrolyte, such as water. An electric field is used to control the transfer rate of neutral or ionized molecules in solution in the electrolyte through the membrane in response to an applied external electromotive force. By adjusting the external electromotive force the membrane can be controlled to selectively pass one type of molecule while rejecting other molecules in solution. A separation between molecules of two or more materials in solution in the electrolyte can thus be achieved.

3 Claims, 5 Drawing Figures

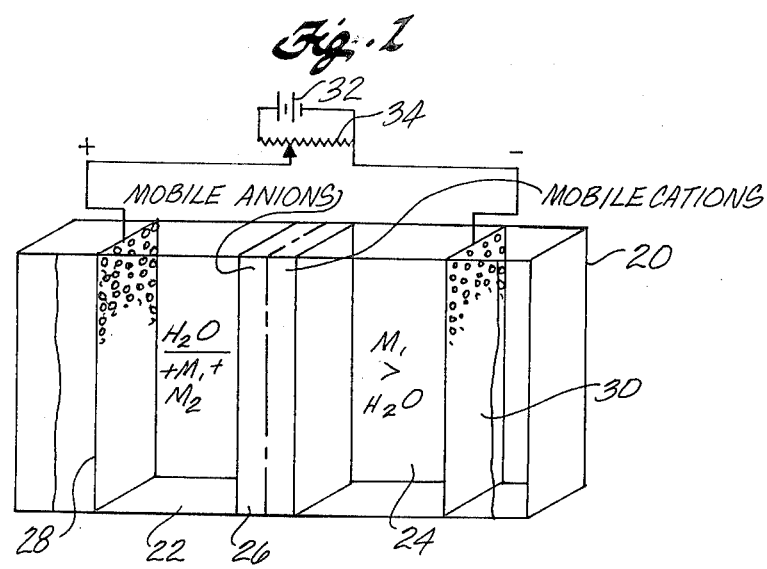
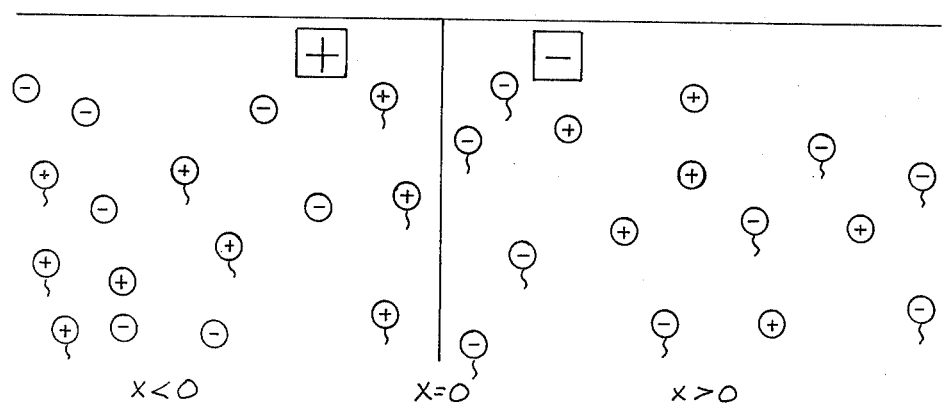

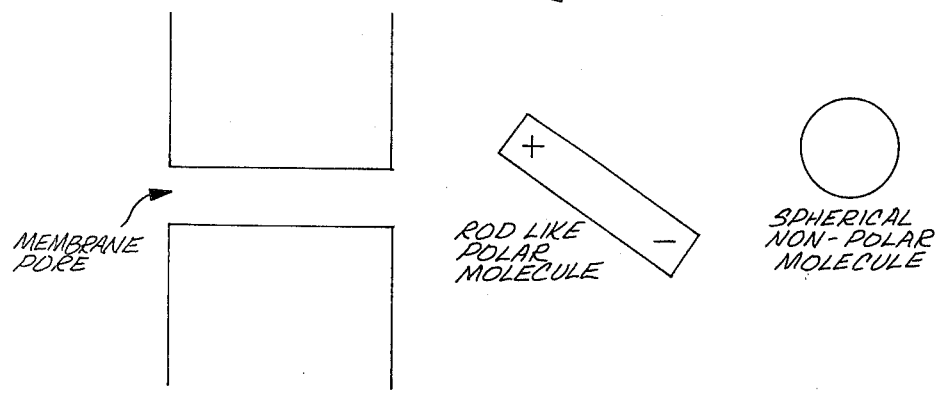
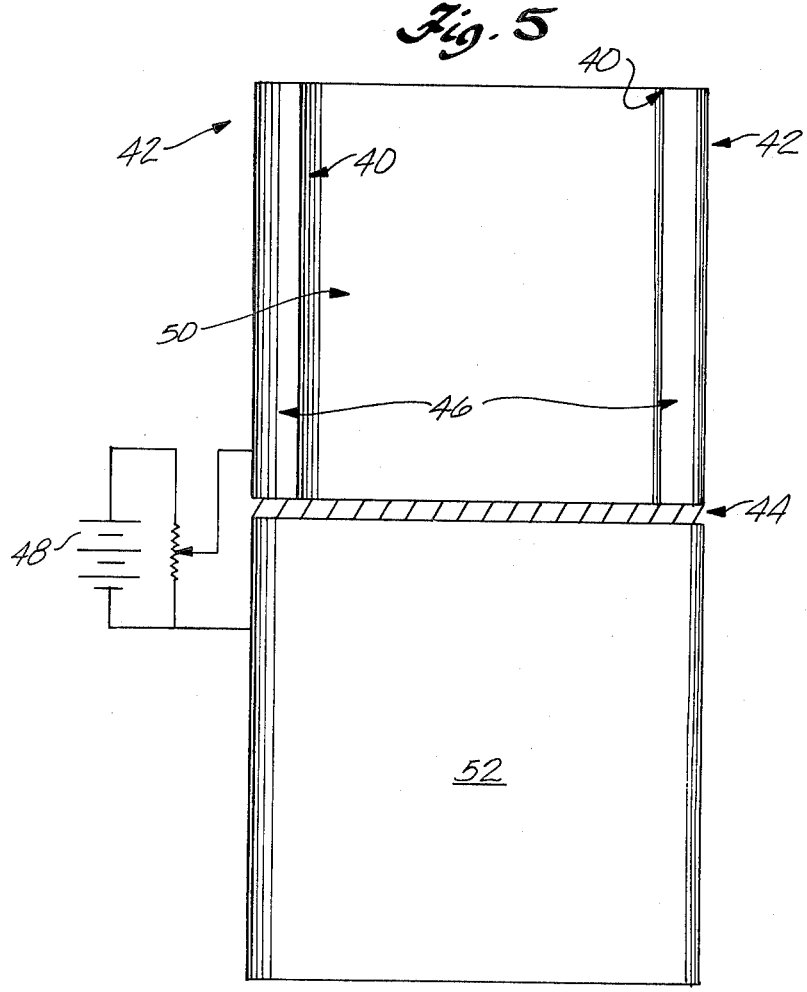

APPARATUS FOR SEPARATING NEUTRAL MOLECULES USING A BIPOLAR MEMBRANE AS A MOLECULAR SIEVE

FIELD OF THE INVENTION

This invention relates to membranes used as molecular filters, and more particularly, is concerned with an apparatus and process utilizing a bipolar type elastic membrane as a molecular sieve, as an electron chonical device (e.g. artificial muscle), as an electroptical device (shutter), and to convert solar to electrical energy.

BACKGROUND OF THE INVENTION

Bipolar membranes exhibit many of the electrical characteristics of a pn-junction. The bipolar membrane has a basic structure comprising two regions consisting of an ion exchange resin. Both regions are of an ionizable species, one region being of a kind which ionizes to yield mobile negative ions and immobile positive ions, while the other region is of the type which ionizes to yield positive mobile ions and negative immobile ions. Diffusion of mobile ions across the junction between the two regions produces a space charge region which is substantially free of mobile ions. The bipolar membrane in terms of its electrical characteristics has been analyzed in the prior art literature. See, for example, the article "Voltage Current Characteristics of Bipolar and Three-Layer Fixed Charge Membranes" by R. Simons, Biochimica Et Biophysics, Acta, 282 (1972) pages 72–79; "Space Charged Regions, Fixed Charge Membranes and the Indicated Property of Capacitance" by A. Mauro, Biophysical Journal 2: 179 (1962). Such bipolar membranes have been constructed by pressing together two strong acid and strong base membranes into a sandwich. A novel method of preparing a sandwich-type bipolar membrane is reported in Chemical Abstracts, Vol. 81, 176899 m (1974), where a conventional ion-selective membrane, of either the cationic or anionic type, is placed in an electrolytic cell with a finely ground ion exchange resin of the opposite selectivity, and a d.c. current applied across the cell to firmly coat the membrane with resin. More recently, a monolithic bipolar membrane has been produced in a single sheet of polyethylene which is hydrolyzed on one side by an NaOH solution in water and is aminated on the other side by a diamine or a polyamine. Such a bipolar membrane is described in detail in the article "Bipolar Membranes Made of a Single Polyolephine Sheet" by F. de Korosy and E. Zeigerson, Israel Journal of Chemistry, Vol. 9, 1971, pp. 483–497. With a cellulosic, non-ion exchange membrane and with a sodium styrene sulfonate ion exchange membrane, the selectivity for thiourea and urea has been changed by physically stretching the membrane, see M. E. Bogdanov and A. A. Efendiev, *Ajob. Khim, Zh.* 4:103, (1975).

SUMMARY OF THE INVENTION

The present invention is directed to the use of bipolar membranes as an electromechanical device, and more particularly, as a molecular sieve which can be controlled by an externally applied electric field to selectively pass neutral molecules of different materials. Specifically, it has been determined that a bipolar membrane having, at best, the elastic characteristics of a rubber may become strained and distorted by application of an external electric field across the membrane. Porosity control, by the present invention, can also be achieved with membranes which are much less elastic than an ideal rubber. This effect can be used to control the migration of molecules of different materials through the membrane by changing the selectivity.

In brief, the present invention provides a molecular sieve for separating differing species of neutral molecules comprised of a bipolar membrane of an elastomeric material immersed in a medium comprising an electrolyte or a polar solvent, such as water or liquid ammonia, the membrane separating the medium into two isolated regions. Electrodes immersed in the medium or either side of the membrane are used to apply an electric field across the membrane. So that electrical contact between the electrodes and the membrane can be made, the medium should have some minimal conductivity. High conductivity, however, is unnecessary, since the separation of neutral species does not depend primarily on the flow of electrical current but only upon applicability of a potential. By adjusting the magnitude of the electric field, the membrane material within the space charge region can be compressed or expanded. Changing the compressive state changes the solvent content of the membrane, its pore size distribution, and the ability of molecules in solution to pass through the membrane by diffusion. Molecules of different materials in solution in the medium on one side of the membrane can thus be isolated with variable controllable selectivity by being allowed to pass into the medium on the opposite side of the membrane. The control of the applied field affects the selectivity of the separation between two or more materials in solution, or provides a valving action for a single material in solution.

BRIEF DESCRIPTION OF THE DRAWINGS

For a more complete understanding of the invention reference should be made to the accompanying drawings, wherein:

FIG. 1 is a schematic showing of an apparatus incorporating the present invention;

FIG. 2 is a diagrammatic showing of bipolar membrane junction;

FIG. 4 is a diagram showing one effect of orientation of a polar molecule in a field; and FIG. 5 is a side view diagram of an apparatus for separating gases by means of the present invention.

DETAILED DESCRIPTION

Figure 3:
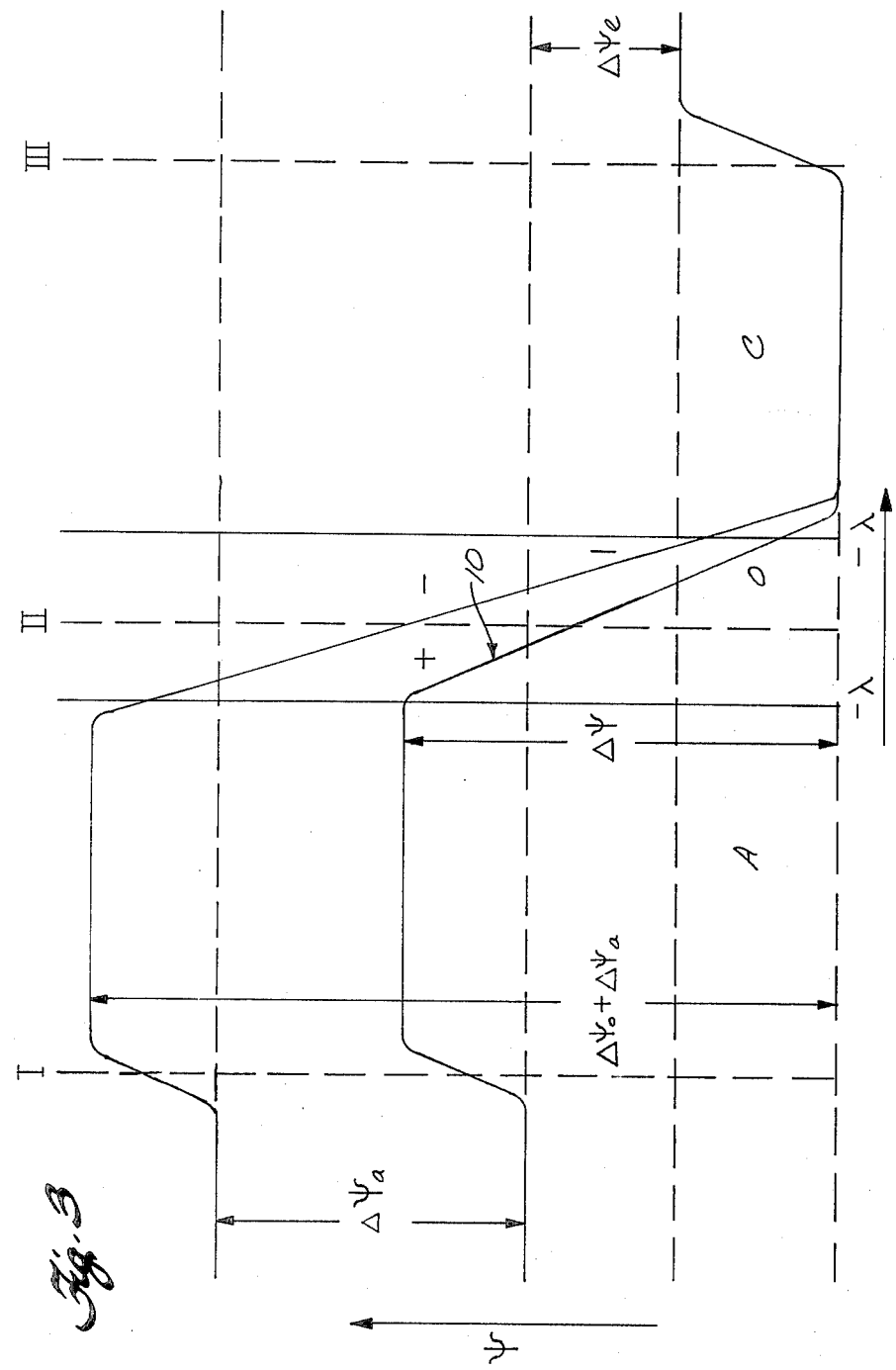
FIG. 3 is a diagram showing the potential distribution within the bipolar membrane.

FIG. 1 illustrates an apparatus which can be used in the present invention and is discussed more fully later.

Referring to FIGS. 2 and 3, there is illustrated in FIG. 2 schematically a small section of a monolithic bipolar membrane of the type described, for example, in the above-identified article by de Korosy. The ideal monolithic bipolar membrane has two regions extending on either side of an imaginary plane, indicated at 10 in FIG. 3 and located at $x=0$. In actual practice graded distributions of anionic and cationic groups can be used in the present invention. One region is formed of an ionizable resin species which yields mobile negative ions, that is, anionic counter ions, shown as the region for which the position coordinate is $x<0$. The other species ionizes to yield mobile positive ions, that is, cationic counterions, shown as the region where the position coordinate is $x>0$. Thus a junction is formed at the place 10 between the two regions. The first species also contains fixed or pendant ions which are positive in the region $x<0$, while the second species comprises pendant negative ions in the region $x>0$. These pendant or fixed ions are attached to the backbone of the membrane structure. In FIG. 2 the fixed pendant ions are shown with "tails" while the mobile counterions are indicated by circles without tails. It will be noted that because the mobile ions of each region can diffuse out of their respective regions until the field generated by this charge transfer halts the process, there is produced a region on either side of plane 10 in FIG. 3 which is depleted in mobile ions. This produces + and − space charges on either side of the plane 10 as indicated in the two squares in FIG. 2. In FIG. 3 the boundaries of this space charge region (which as an approximation are shown as abrupt) are indicated at $-\lambda$ and $+\lambda$. The width of this "double layer" space charge region depends on the voltage across the junction and vice versa.

When the membrane is immersed in an aqueous solution, the membrane becomes swollen by the absorption of water and the mobile counterions are contained within this absorbed water. The absorbed water (or other solvent) may usually be considered as occupying pores in the membrane structure. FIG. 3 shows a plot of the variation in the electrical potential through a cross-section of the bipolar membrane immersed in water. The vertical lines at 12 and 14 represent the outer boundaries of the bipolar membrane and the surrounding water. The region in the membrane indicated by A represents the region of anionic counterions, while the region indicated at C represents the region of cationic counterions.

It will be seen from FIG. 3 that the electrical potential varies with position x as indicated by the curve marked "0". The curve marked "1" indicates the variation of potential when an external potential $\Delta\psi_a$ is applied in the "reverse" direction across the membrane, that is, the direction in which the mobile ions on each side of the junction are driven away from the junction by the applied field so as to widen the depletion region and reduce the conductivity of the membrane. It will be seen that the bipolar membrane has many of the characteristics of a PN-junction. Thus increasing the potential in the reverse direction, by widening the depletion region $-\lambda$ to $+\lambda$, increases the resistance and the capacitance of the junction. With a potential applied in the forward direction most of these effects are inverted and the junction becomes conductive to current flow by the "injection" across the junction of co-ions (or minority carriers) whose fluxes are determined by diffusion alone.

It is worthwhile to provide a schematic of the variation of the electrical potential throughout this system for the case where the Donnan potential is not overwhelmed. FIG. 2 serves this purpose. In the Figure the three junctions, I, II, and III, are between external solution and anionic membrane, anionic and cationic membrane (the junction), and cationic membrane and external solution respectively. The anionic and cationic membranes are indicated by the letters A and C. The solid vertical lines, labeled $-\lambda$ and $\lambda$ respectively are the (approximately defined) boundaries, in the absence of an applied potential, of the depletion layer (typical of a p,n-junction) in which there are negligible concentrations of mobile ions and where the + and − space charges (indicated by + and − in the Figure) are due to the fixed ions.

Electrical potential $\psi$ increases vertically in the Figure and with no external applied potential its variation with position x is indicated by the solid curve labeled 0. The first change in potential, due to the Donnan phenomenon, occurs at interface I and is positive. The "bipolar" potential variation $\Delta\psi_o$ occurs at interface II and is negative. The variation at interface III is again Donnan in origin and is positive. The total variation in potential is denoted by $\Delta\psi_e$ and would in fact vanish if the solution was the same on both sides of the membrane.

The curve labeled 1 indicates the variation of potential when an external potential, $\Delta\psi_a$, is applied to the system in the "reverse" direction. The reverse direction corresponds to the high resistance branch of the rectifying characteristic and in this direction the mobile ions on each side of the junction are driven away from the junction widening the depletion region (increasing the magnitude of $\lambda$) and requiring that the current in the depletion region (which is rate controlling) be carried, for example, when water is the medium, by $H^+$ and $OH^-$ ions derived by the "splitting" of water. The widened depletion region is not explicitly delineated in the Figure but can be discerned from the increased breadth of the sloped region of curve 1 in the neighborhood of the junction.

The monolithic membrane material is elastomeric, exhibiting some of the elastic properties of rubber, for example. The intense field produced by the potential change across the double-layer space charge region − to + operates to exert a physical stress on the polymer material through its action on the pendant ions. Referring to FIG. 2, it can be seen that in the neighborhood of the junction the material on the left ($x<0$) will be "pulled" by the electric field toward the right, while the opposite will be true of the material on the right of the junction. This effect occurs only within the space charge layer between $x=-\lambda$ and $x=+\lambda$. As a result the elastomeric material of the bipolar membrane within the space charge layer is physically compressed in the x direction and the strain or deformation is a function of x. The material of the membrane outside of the space charge layer remains unstrained but the part to the left of $x=-\lambda$ will be translated to the right, while the part to the right of the $x=+\lambda$ will be translated to the left. If an external field is applied which produces a potential in the "forward" direction, the compressive effect is reduced and if an external field is applied which is in the "reverse" direction, the compressive effect is enhanced.

While the physically measurable changes in the thickness of the membrane are small, being under the best conditions on the order of 0.15 microns with an applied field potential of 10 volts, substantial effects on the ability of the membrane to pass, reject, and discriminate among neutral molecules with small changes in the applied field are possible. As shown in FIG. 1, a tank 20 is divided into two compartments 22 and 24 by a bipolar membrane 26 of elastomeric material, such as described above. The tank is filled with a medium, such as water, on both sides of the membrane. An electric field is applied across the membrane by a pair of electrodes 28 and 30 which are connected to a variable DC voltage source. The source is shown schematically as a battery 32 and potentiometer 34 but any DC potential source may be used having a voltage range of the order of 0-100 volts. The polarity of the external field as applied to the junction is in the "reverse" direction, that is, in the direction which reduces the number of mobile ions in the double layer or space change region. However, the polarity of the field may also be applied in the forward direction to further reduce the compression effect on the space charge region due to the internal field in the space charge region, which accounts for a potential difference on the order of 0.7 volts.

If the neutral molecules (e.g. urea and thiourea) are placed in solution in the water on one side of the membrane, the molecules will migrate through the membrane as part of the water "swelling" the membrane. As the applied field is increased in the reverse direction across the membrane, the pore size distribution in the membrane is changed. Also some water is squeezed out of the double layer region by the compressive effect described above. Furthermore there can be an orientational effect on polar neutral molecules (see FIG. 4). At the same time the double layer region develops an altered, selective permeability to the neutral molecules in solution in the water. Thus the selective transfer rate of molecules through the membrane, i.e., the porosity of the membrane, can be controlled by merely adjusting the level of the applied field. This response is different for different molecules. The bipolar membrane may therefore be considered as a molecular sieve or separator where selectivity can be adjusted by the level of the applied field.

FIG. 4, herein, illustrates a possible situation in which the field can assist the separation of a rod-like molecule with a dipole moment from a more spherical non-polar molecule. Even if the pore size is not changed by the field, the partial orientation of the rod-like molecule by the field can enable it to slip through the pore where the spherical molecule cannot. This emphasizes the fact that more than changes in pore shape and size distribution can be involved in the separation of certain molecular species.

The apparatus of FIG. 1 may be used to separate molecules of different materials in solution. By placing the solution in the compartment on one side of the membrane with an applied voltage in the reverse direction, the membrane will most often but not always (depending on the molecules) operate to block migration of the molecules into the second compartment on the opposite side of the membrane. By reducing the level of the field in the reverse direction a level can be found at which one of the materials in solution will be selectively passed by the membrane so that the one material will be more concentrated in the second compartment relative to the other materials in solution. This process can be repeated in successive stages at different potential levels to provide separation of other materials from the same solution.

An apparatus can be constructed for using the membranes to separate components of a gas mixture. In FIG. 5, for example, one cylindrical tube 40 may be placed within another cylindrical tube 42 of somewhat larger diameter and a bipolar membrane 44 attached to one end of both cylinders. A suitable liquid medium introduced into the space between the walls of the two cylinders 46 can be used to wet the membrane. When a voltage 48 is applied across the membrane, it can be used to selectively separate gases which are introduced into the inner cylinder 50, the desired component either being retained by the membrane or being passed through the membrane into a receptacle 52.

The physical compressive effect of an applied field on the double layer region of the bipolar membrane is not only useful in a process for separating materials, but the electromechanical properties of the membrane suggest that it can be applied to many applications as a transducer for converting mechanical energy into electrical energy, or electrical energy into mechanical energy, e.g. to fabricate an artificial muscle and there are other applications.

The water splitting capability of the bipolar membrane can be coupled to an electrode system sensitive to the redox equilibrium of a dye system so that solar energy may be used to split water and store energy in the resulting acid and base product. The water splitting configuration, operated then in reverse can be made to deliver the energy because it functions as a primary battery. In another application the electromechanical effect which forms the central mechanism of the separations scheme discussed in this application can also be used to convert electrical energy directly into mechanical work or vice versa.

In still another application the strong field of the depletion region at the junction should give rise to interesting optical effects (polarization) and can provide an electrically controllable "shutter". The same strong field can be applied to a lightly cross-linked membrane which can then be more fully cross-linked by soft electrons or uv radiation while the applied field was maintained, in some cases, with formation of a permanent electret of greater strength when the applied field is removed. Finally a "mosaic" bipolar structure can be made such that application of an external potential will produce an instantaneous change in the effective elastic modulus of a macroscopic member. A substance with such an electrically controlled modulus can be useful in constructing artificial muscles.

While the apparatus of FIG. 1 illustrates the use of a single membrane to selectively pass one material in solution, the apparatus could be made with any number of membranes arranged in stages to separate a number of different materials in solution, each stage selectively blocking one constituent and passing the balance of materials. Materials that produce neutral molecules in solution and are subjected to controlled diffusion through the bipolar membrane include acetone, acetic acid, salmine sulfate, sucrose, and urea. Many other materials of course, both neutral and ionized molecules in solution, can be separated by this process.

Many uses have been developed with membranes having a fixed porosity for the separation of soluble or colloidal species from solutions, and the bipolar membranes of this invention can be used in similar applications with improved performance.

A well-known use for membrane materials is in the field of water desalting by the technique known as reverse osmosis. This process is described, for example, in Chemical Week, Aug. 30, 1969, page 33, reporting on a plant producing water of less than 500 ppm dissolved solids from brackish water of more than 2000 ppm dissolved solids.

In the field of sugar processing, membrane separations have been used as reported in Chemical Technology, October, 1971, page 636. One application is the recovery of xylose from pulp mill wastes, in which a membrane is used which will pass xylose molecules but retain such impurities as lignins, gums and other colloidal materials. Another example is the purification of sucrose solutions prior to the crystallization step in the process: polysaccharides, lignins, proteins, starches, gums and other colloidal material will not pass through the particular membrane chosen, but sucrose molecules are transported through the membrane.

Several separations using specific membranes are listed in Chemical Engineering Progress, Vol. 64, page 31 (1968), as shown in the following table:

| Membrane | Species (Molecular Weight) | % Retained |
|---|---|---|
| Diaflo UM-10 | Raffinose (594) | 0 |
| Diaflo UM-10 | Dextran (10,000) | 100 |
| Diaflo UM-05 | Sodium Chloride | 5 |
| Diaflo UM-05 | Sucrose | 90 |
| Diaflo XM-50 | Dextran (10,000) | 0 |
| Diaflo XM-50 | Bovine Serim Albumin (69,000) | 100 |
| Diaflo XM-100 | Human Serum Albumin (69,000) | 0 |
| Diaflo XM-100 | Gamma Globulin (160,000) | 100 |

All of these separations can be made by means of the process and apparatus described herein.

What is claimed is:

1. A molecular separator with electrically adjustable controlled selectivity for separating a neutral molecule from solution comprising: a porous bipolar membrane of an elastomeric material, means for applying an electric field across the membrane, means for adjusting the porosity of such bipolar membrane which comprises means for varying the magnitude of the electric field, means for applying a solution containing such neutral molecule to one side of the membrane, and means for applying a solvent to the other side of the membrane for receiving such neutral molecule selectively passed by the bipolar membrane.

2. Apparatus of claim 1 wherein the bipolar membrane comprises a single sheet of a polyolefin material treated to provide a cation selective region and an anion selective region.

3. Apparatus of claim 1 wherein the bipolar membrane is immersed in an aqueous solution.

* * * * *

UNITED STATES PATENT AND TRADEMARK OFFICE
CERTIFICATE OF CORRECTION

PATENT NO. : 4,225,412
DATED : September 30, 1980
INVENTOR(S) : Howard (nmi) Reiss It is certified that error appears in the above—identified patent and that said Letters Patent is hereby corrected as shown below:

Column 1, line 10, "electron chonical" should be ---electromechanical---.

Column 1, line 11, "electroptical" should be --electro-optical--.

Column 2, line 12, "or" should be --on--.

Signed and Sealed this

Twenty-seventh Day of January 1981

[SEAL]

Attest:

RENE D. TEGTMEYER

Attesting Officer     Acting Commissioner of Patents and Trademarks